(12) United States Patent
Mase et al.

(10) Patent No.: US 8,211,683 B2
(45) Date of Patent: Jul. 3, 2012

(54) PLASMID, TRANSFORMANTS AND PROCESS FOR PRODUCTION OF 3-CARBOXYMUCONOLACTONE

(75) Inventors: Kohei Mase, Kariya (JP); Toshihisa Shimo, Kariya (JP); Naoki Ohara, Kariya (JP); Yoshihiro Katayama, Tokyo (JP); Kiyotaka Shigehara, Tokyo (JP); Eiji Masai, Nagaoka (JP); Masao Fukuda, Nagaoka (JP); Seiji Ohara, Tsukuba (JP); Masaya Nakamura, Tsukuba (JP); Yuichiro Otsuka, Tsukuba (JP)

(73) Assignees: Kabushiki Kaisha Toyota Jidoshokki, Aichi-Ken (JP); National University Corporation, Tokyo University of Agriculture and Technology, Tokyo (JP); Nagoya University of Technology, Niigata (JP); Forestry and Forest Products Research Institute, Ibaraki (JP)

( * ) Notice: Subject to any disclaimer, the term of this patent is extended or adjusted under 35 U.S.C. 154(b) by 451 days.

(21) Appl. No.: 12/310,095

(22) PCT Filed: Aug. 10, 2007

(86) PCT No.: PCT/JP2007/065989
§ 371 (c)(1),
(2), (4) Date: Sep. 29, 2009

(87) PCT Pub. No.: WO2008/018640
PCT Pub. Date: Feb. 14, 2008

(65) Prior Publication Data
US 2010/0075388 A1 Mar. 25, 2010

(30) Foreign Application Priority Data
Aug. 10, 2006 (JP) ................................. 2006-218524

(51) Int. Cl.
*C12N 9/00* (2006.01)
*C12N 15/00* (2006.01)
*C12N 1/20* (2006.01)

(52) U.S. Cl. .................. 435/183; 435/320.1; 435/252.3

(58) Field of Classification Search .................. 435/183, 435/320.1, 252.3
See application file for complete search history.

(56) References Cited

U.S. PATENT DOCUMENTS
5,616,496 A 4/1997 Frost et al.

FOREIGN PATENT DOCUMENTS
JP 2005-278549 10/2005
WO WO 01/07629 2/2001

OTHER PUBLICATIONS

Frazee RW, et al, "Cloning, sequencing, and expression of the *Pseudomonas putida* protocatechuate 3, 4-dioxygenase genes", *J. Bacteriol.*, 1993, vol. 175, No. 19, p. 6194-6202.

Parke, D. "Positive selection for mutations affecting bioconversion of aromatic compounds in Agrobacterium tumefaciens: analysis of spontaneous mutations in the protocatechuate 3, 4-dioxygenase gene"; *J. Bacteriol*, 2000, vol. 182, No. 21 p. 6145-6153.

PCT International Search Report PCT/JP2007/065989, mailed Sep. 11, 2007.

Priefert, H. et al, "Molecular characterization of genes of *Pseudomonas* sp. Strain HR 199 involved in bioconversion of vanillin to protocatechuate", *J. Bacteriol.*, 1997, vol. 179, No. 8, p. 2595-2607.

Dirk Eulberg, et al., "Characterization of a Protocatechuate Catabolic Gene Cluster from *Rhodococcus opacus* 1CP: Evidence for a merged Enzyme with 4-Carboxymuconolactone-Decarboxylating and 3-Oxoadipate Enol-Lactone-Hydroloyzing Activity", Journal of Bacteriology, Mar. 1998, vol. 180, No. 5, pp. 1072-1081.

European Search Report for Application No. 07792616.0-2406/2048231 (PCT/JP2007065989), issued Jan. 7, 2010.

*Primary Examiner* — Maryam Monshipouri
(74) *Attorney, Agent, or Firm* — Locke Lord LLP

(57) ABSTRACT

There is provided a process for industrial production of simple 3-carboxy-cis,cis-muconic acid and/or 3-carboxymuconolactone from low molecular mixtures derived from plant components such as vanillin, vanillic acid and protocatechuic acid, via a multistage enzyme reaction. A recombinant plasmid containing a vanillate demethylase gene (vanAB genes), benzaldehyde dehydrogenase gene (ligV gene) and protocatechuate 3,4-dioxygenase gene (pcaHG genes); transformants incorporating the plasmid; and a process for production of 3-carboxy-cis,cis-muconic acid and/or 3-carboxymuconolactone characterized by culturing the transformants in the presence of vanillin, vanillic acid, protocatechuic acid or a mixture of two or more thereof.

7 Claims, 4 Drawing Sheets

SEQUENCE LISTING

<160> NUMBER OF SEQ ID NOS: 8

<210> SEQ ID NO 1
<211> LENGTH: 720
<212> TYPE: DNA
<213> ORGANISM: Pseudomonas putida KT2440

<400> SEQUENCE: 1

```
atgcccgccc aggacaacag ccgcttcgtg atccgtgatc gcaactggca ccctaaagcc      60
cttacgcctg actacaagac ctccgttgcc cgctcgccgc gccaggcact ggtcagcatt     120
ccgcagtcga tcagcgaaac cactggtccg gacttttccc atctgggctt cggcgcccac     180
gaccatgacc tgctgctgaa cttcaataac ggtggcctgc ccattggcga gcgcatcatc     240
gtcgccggcc gtgtcgtcga ccagtacggc aagcctgtgc cgaacacttt ggtggagatg     300
tggcaagcca acgccggcgg ccgctatcgc cacaagaacg atcgctacct ggcgcccctg     360
gacccgaact tcggtggtgt tgggcggtgt ctgaccgacc gtgacggcta ttacagcttc     420
cgcaccatca agccgggccc gtacccatgg cgcaacggcc cgaacgactg gcgcccggcg     480
catatccact tcgccatcag cggcccatcg atcgccacca agctgatcac ccagttgtac     540
```

| | |
|---|---|
| ttcgaaggtg acccgctgat cccgatgtgc ccgatcgtca agtcgatcgc caacccgcaa | 600 |
| gccgtgcagc agttgatcgc caagctcgac atgagcaacg ccaacccgat ggactgcctg | 660 |
| gcctaccgct ttgacatcgt gctgcgcggc cagcgcaaga cccacttcga aaactgctga | 720 |

<210> SEQ ID NO 2
<211> LENGTH: 239
<212> TYPE: PRT
<213> ORGANISM: Pseudomonas putida KT2440

<400> SEQUENCE: 2

```
Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser Val Ala Arg Ser
                20                  25                  30

Pro Arg Gln Ala Leu Val Ser Ile Pro Gln Ser Ile Ser Glu Thr Thr
            35                  40                  45

Gly Pro Asp Phe Ser His Leu Gly Phe Gly Ala His Asp His Asp Leu
        50                  55                  60

Leu Leu Asn Phe Asn Asn Gly Gly Leu Pro Ile Gly Glu Arg Ile Ile
65                  70                  75                  80

Val Ala Gly Arg Val Val Asp Gln Tyr Gly Lys Pro Val Pro Asn Thr
                85                  90                  95

Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
        115                 120                 125

Arg Cys Leu Thr Asp Arg Asp Gly Tyr Tyr Ser Phe Arg Thr Ile Lys
    130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Gln Leu Ile Ala Lys
        195                 200                 205

Leu Asp Met Ser Asn Ala Asn Pro Met Asp Cys Leu Ala Tyr Arg Phe
    210                 215                 220

Asp Ile Val Leu Arg Gly Gln Arg Lys Thr His Phe Glu Asn Cys
225                 230                 235
```

<210> SEQ ID NO 3
<211> LENGTH: 606
<212> TYPE: DNA
<213> ORGANISM: Pseudomonas putida KT2440

<400> SEQUENCE: 3

| | |
|---|---|
| atgccaatcg aactgctgcc ggaaaccct tcgcagactg ccggcccta cgtgcacatc | 60 |
| ggcctggccc tggaagccgc cggcaacccg acccgcgacc aggaaatctg gaactgcctg | 120 |
| gccaagccag acgccccggg cgagcacatt ctgctgatcg ccacgtata tgacggaaac | 180 |
| ggccacctgg tgcgcgactc gttcctggaa gtgtggcagg ccgacgccaa cggtgagtac | 240 |
| caggatgcct acaacctgga aaacgccttc aacagctttg gccgcacggc taccaccttc | 300 |
| gatgccggtg agtggacgct gcaaacggtc aagccgggtg tggtgaacaa cgctgctggc | 360 |
| gtgccgatgg cgccgcacat caacatcagc ctgtttgccc gtggcatcaa catccacctg | 420 |

```
cacacgcgcc tgtatttcga tgatgaggcc caggccaatg ccaagtgccc ggtgctcaac    480
ctgatcgagc agccgcagcg gcgtgaaacc ttgattgcca agcgttgcga agtggatggg    540
aagacggcgt accgctttga tatccgcatt caggggaag gggagaccgt cttcttcgac     600
ttctga                                                               606
```

<210> SEQ ID NO 4
<211> LENGTH: 201
<212> TYPE: PRT
<213> ORGANISM: Pseudomonas putida KT2440

<400> SEQUENCE: 4

```
Met Pro Ile Glu Leu Leu Pro Glu Thr Pro Ser Gln Thr Ala Gly Pro
1               5                   10                  15

Tyr Val His Ile Gly Leu Ala Leu Glu Ala Ala Gly Asn Pro Thr Arg
            20                  25                  30

Asp Gln Glu Ile Trp Asn Cys Leu Ala Lys Pro Asp Ala Pro Gly Glu
        35                  40                  45

His Ile Leu Leu Ile Gly His Val Tyr Asp Gly Asn Gly His Leu Val
    50                  55                  60

Arg Asp Ser Phe Leu Glu Val Trp Gln Ala Asp Ala Asn Gly Glu Tyr
65                  70                  75                  80

Gln Asp Ala Tyr Asn Leu Glu Asn Ala Phe Asn Ser Phe Gly Arg Thr
                85                  90                  95

Ala Thr Thr Phe Asp Ala Gly Glu Trp Thr Leu Gln Thr Val Lys Pro
            100                 105                 110

Gly Val Val Asn Asn Ala Ala Gly Val Pro Met Ala Pro His Ile Asn
        115                 120                 125

Ile Ser Leu Phe Ala Arg Gly Ile Asn Ile His Leu His Thr Arg Leu
    130                 135                 140

Tyr Phe Asp Asp Glu Ala Gln Ala Asn Ala Lys Cys Pro Val Leu Asn
145                 150                 155                 160

Leu Ile Glu Gln Pro Gln Arg Arg Glu Thr Leu Ile Ala Lys Arg Cys
                165                 170                 175

Glu Val Asp Gly Lys Thr Ala Tyr Arg Phe Asp Ile Arg Ile Gln Gly
            180                 185                 190

Glu Gly Glu Thr Val Phe Phe Asp Phe
        195                 200
```

<210> SEQ ID NO 5
<211> LENGTH: 24
<212> TYPE: DNA
<213> ORGANISM: Artificial Sequence
<220> FEATURE:
<223> OTHER INFORMATION: universal primer

<400> SEQUENCE: 5

```
ggtgtcaggc aaaggtgtta agac                                           24
```

<210> SEQ ID NO 6
<211> LENGTH: 24
<212> TYPE: DNA
<213> ORGANISM: Artificial Sequence
<220> FEATURE:
<223> OTHER INFORMATION: reverse primer

<400> SEQUENCE: 6

```
ggtgtcaggc aaaggtgtta agac                                           24
```

<210> SEQ ID NO 7
<211> LENGTH: 2117
<212> TYPE: DNA
<213> ORGANISM: Pseudoalteromonas putida PpY101

<400> SEQUENCE: 7

```
ggagagcctc atgtacccga gaaacacttg gtacgtcgcc tgcaccccg atcgagatcg      60
ccaccaaacc cctgggccgg cagatctgcg gggaaaaaat cgtgttctac cgcgcccgcg     120
agaaccaagt agccgccgtc gaggacttct gcccgcaccg cgcgcaccgt tgtcgttggg    180
ctatgtcgag gacggcaacc tggtgtgcgc ctaccacggc ctggtgatgg gttgcgacgg    240
caagaccgtg tcgatgccgg gccaacgggt gcgtggcttc ccctgcaaca agacctttgc    300
ggccgtcgag cgctatggct tcatctgggt ctggcccgt gaccaggcgc aggccgaacc     360
cggcctgatt ccgcatctgg aatgggcggt gagtgatgag tgggcctacg gcggcgggct    420
gttccacatc ggttgcgact accgctgat gatcgacaac ctcatggacc tcacccatga     480
aacctatgtg cacgcctcca gcatcggcca gaaggagatc gacgaggcac cgccgtacca    540
ccgtcaccgg cgacgaatgg tcaccgcccg gcacatggaa aacatcatgg cgccaccgtt    600
ctggcgcatg gccttgcgtg gcaatggcct ggccgacgat gtaccagtgg accgctggca    660
gatctgccgt tcaccccac ctagccatgt gctgatcgaa gtgggtgtag cgcatgccgg     720
caagggcggc taccacgccg aggcacagca taaggcgtcg agcatcgtgg tcgacttcat    780
caccccctgag agcgatacct ctatctggta cttctggggc atggcgcgca acttcgctgc    840
gcacgaccag accctgaccg acaacattcg tgagggccag ggcaagattt tcagcgaaga    900
cctggaaatg ctcgaacgcc agcagcagaa cctgctgccc caccccgagc gcaacttgct    960
gaagctgaat atcgacgccg gcgtgcagtc acgcaaagtg ctggagcgga tcatcgccca   1020
agagcgtgcg ccgcagccgc aactgatcgc caccagcgcc aaccctgcct gaggaacagc    1080
cgacatgatc gatgccgtag tggtatcccg taacgatgaa gcgcagggta tctgcagctt   1140
cgagctggcc ccggcagatg gcagcctgct gcgggccgtt cacgcgcccc atatcgacgt    1200
gcaccttccc gaacggtggt ccaattattc gctgtgcaac caccccgaag aacgccatcg    1260
ctatctgatt ggcgtactca acgaccggct tcgcggggcg gtttctcgta gctgcacgaa    1320
cagggttgca gacgtggccc gggtgcgtat cagtgcgccg cgcaaccctg ttcccgctgg    1380
ccgagggtgc gcagcgcagt ttgctgtttg ctggcggtat cgacattacc ccaatccctg    1440
tgcatggcsg agcagctgtc ccaacagcgg ccaggccttc gagctgcact actgtgcccg    1500
ctccagcgag cgtgcggcgt ttgtcgagcg gatccgcagc gcgccgttcg ctgatcggct    1560
gttcgtgcat tttgacgagc agtcggaaac ggcgctggac atcgcccagg tgctgggcaa    1620
cccgcaagat gatgtgcacc tgtatgtatg cgggcccggc gggttcatgc agcatgtgct    1680
ggacagcgcg aaggggctgg gctggcagga ggccaacctg caccgcgagt acttcgccgc    1740
agcaccggtg gatgccagca acgatggcag tttcgcggtg caggtgggca gcacgggaca    1800
ggtgttcgag gtgccagccg accggaccgt ggtgcaggtg ctggaagaga atggtatcga    1860
gatcgccatg tcgtgcgagc agggtatttg cggcacctgc ctgacacgcg tgctgcaggg    1920
cacaccggac catcgcgatc tgtttctcac cgaagaggaa caggccctga cgatcagtt    1980
cacgccctgc tgctcgcgct cgaagacgcc gctgctggtg ctggacatct gactccttac    2040
gacgagggca ggatgacttt catgcccgcg tctgccgcag ccccgccaaa ggtttcggca    2100
taacgcaagg tggcatt                                                  2117
```

<210> SEQ ID NO 8
<211> LENGTH: 2094
<212> TYPE: DNA
<213> ORGANISM: Sphingomonas pauciobilis SYK-6

<400> SEQUENCE: 8

```
cccgggccag atgcgcccgg cgctgcctcc cggtcaagtc gacattcccc ctcacggtca      60
agcggggcgg gcatccagtg cagcaatgcc ggccgacatg acaattccca tgccttcaca     120
ctggacttga gcgggagtcg cggcaagaag gtccccgtca atggactcag cgcggatcgc     180
gccagaccag gagagagaca gaatggaatt tacccggctt aaccccatga ccggcgaagt     240
cgcttcgtcg gcgcccgcgc tcaaggcggg tgacattccc gcgatcgccc gcaaggcccg     300
cgaaggcttc accgcctggt cggtgatggg ccccaatgcg cgccgcgccg tgctgatgaa     360
agccgcgacg gcgctggaag cccgcgcgga cgcgttcgtc gatgcgatga tgggagagat     420
cggcgccacc aagggctggg ctctgttcaa tctcggactg gcggccagca tggtgcgcga     480
ggcagcggcc ctgacgacgc agatcaatgg cgaagtcatc ccctccgaca agcccggctg     540
cctcgccatg gcgctgcgcg aaccggtggg cgtcattctc ggcatcgcgc cctggaatgc     600
gccgatcatc ctcggcgtgc gcgccatcgc cgtgccgctg gcttgcggca acagcgtgat     660
cctgaaggcg agcgagacct gcccgcgcac ccatgccctc atcatcgagg cattcgcaga     720
tgcggggttc cccgagggag tcgtcaacgt cgtcaccaat gcgccagccg atgcgggcga     780
agtggtcggc gcgctgatcg acgcgccgga agtcaagcgg atcaatttca ccggctccac     840
cggggtcggc aagatcatcg ccaagcgtgc cgccgagcat ctcaagcccg tgctgctgga     900
gctgggtggc aaagccccgc tcattgtcct ggaggacgcc gatctggatg aagccgtcaa     960
ggcggccgcc ttcggcgctt tcatgaacca ggggcagatc tgcatgtcca cggagcggat    1020
catcgtggtg gatgcggtgg ccgacgaatt cgccgcccgg ttcaaggcaa aggtttcggc    1080
catgcctgtt ggcgatcccc ggcagggaag cacgccgctg ggagcggtcg tcgacaccaa    1140
gactgtcgcg cattgcctgt ccttgatcga ggatgcgctt ggaaagggcg cggagcagct    1200
gacgggcggc gagacgacgc agaatgtgct gatgccggcg catgtgatcg accgcgtcac    1260
gcccgacatg aagctcttcc gggacgagag cttcggtcct gtcgtgggga tcatccgcgc    1320
acgcgacgcc gagcatgcga tcgaactggc caacgacacc gaatatggtc tctcggcctc    1380
ggtcttcacg cgcgacacgg ccaagggcct cagcgtcgcc cggcggatcg aatccgggat    1440
ctgccatgtc aacgggccga cggtccatga cgaggcgcag atgcccttcg gcggcgtgaa    1500
ggcttcgggc tatggtcgtt tcggcggcaa ggccggcatc gacagcttca cggagctgcg    1560
ctggatcacc atcgagaccc agccgggaca tttcccgatc tgagggcgtc gcgcggccgg    1620
ctcatcgagc cggtcgcgtc cgcagctgcc tggtcgctct cgcgcgctca gggacggctg    1680
atcaggtcca gacgccgacc gctctgcgag acggtcacct catggcgtgc gccggcttgc    1740
gctgccaggg cttcgaagag ggagccgcca aggccgctcc ccgacgtcgc tgccttcgtc    1800
atgtgactgg ctccgccaac gccatcatcc atgatggcaa gctgccaacc attctccgtg    1860
acaaccagcg tgacacgcac ggtgccggcc cgaccttccg gaaaagcgtg cttggcgcaa    1920
ttggtcagtg cctcgttgag ataaagcccc acggctacgg cggccttgcc ggaagcgag    1980
acgtccgtaa gcgcgctttc gatggcgatg cgctcgctga acaggccttc gctgaagcgc    2040
tcgagaagcc gtgcgagata gggcttcatg gcaacctcgc tgctttcccc cggg          2094
```

PLASMID, TRANSFORMANTS AND PROCESS FOR PRODUCTION OF 3-CARBOXYMUCONOLACTONE

This application is a 371 of PCT/JP2007/065989 filed Aug. 10, 2007 which claims priority to Japanese allocation No. 2006-218524 filed Aug. 10, 2006.

FIELD OF THE INVENTION

The present invention relates to a recombinant plasmid comprising genes coding for enzymes participating in a multistage reaction process for fermentative production of 3-carboxy-cis,cis-muconic acid and/or 3-carboxymuconolactone from vanillin, vanillic acid, protocatechuic acid or combinations thereof, which are found in low molecularized mixtures of plant aromatic components, to transformants incorporating the recombinant plasmid, and to a process for industrial production of 3-carboxy-cis,cis-muconic acid and/or 3-carboxymuconolactone using the same.

BACKGROUND OF THE INVENTION

Lignin, a major component of plants, is a biomass resource that is ubiquitously present as an aromatic high molecular compound in plant cell walls. However, since plant-derived aromatic components composed mainly of lignin are composed of components with various chemical structures and have complex macromolecular structures, no effective technology has been developed for their use. The known utilization technologies involve separation and production of vanillin as a material for perfumes, from low molecular aromatic decomposition products of alkaline decomposition or other chemical decomposition of aromatic components. Currently, however, no method is known for effective use of large amounts of low molecular aromatic substances, other than vanillin, that are produced by chemical decomposition. Consequently, lignin produced in mass by paper-making processes has been burned as a substitute for heavy oil, without being effectively utilized.

The present inventors have found that plant aromatic components such as lignin are converted to low molecular mixtures containing vanillin, syringaldehyde, vanillic acid, syringic acid, protocatechuic acid or the like by chemical decomposition methods such as hydrolysis, oxidative decomposition or solvent decomposition, or physicochemical decomposition methods with supercritical water or supercritical organic solvents, and that these five compounds are converted to the single intermediate substance 2-pyrone-4,6-dicarboxylic acid, which can serve as starting materials for functional plastics or chemical products.

The present inventors have also reported a method of producing 2-pyrone-4,6-dicarboxylic acid from vanillin, syringaldehyde, vanillic acid, syringic acid or protocatechuic acid using transformants carrying genes coding for 4 different enzymes (benzaldehyde dehydrogenase, demethylase, protocatechuate 4,5-dioxygenase and 4-carboxy-2-hydroxy-6-semialdehyde muconate dehydrogenase) that participate in a multistage process for fermentative production of 2-pyrone-4,6-dicarboxylic acid (see Japanese Unexamined Patent Publication No. 2005-278549, for example).

However, while numerous intermediates in addition to 2-pyrone-4,6-dicarboxylic acid are known to be obtained by fermentative production from vanillin, syringaldehyde, vanillic acid, syringic acid and protocatechuic acid, their fermentative production processes have not been reported.

SUMMARY OF THE INVENTION

It is therefore an object of the present invention to provide a process for industrial-scale fermentative production of 3-carboxy-cis,cis-muconic acid and/or 3-carboxymuconolactone, as plant-derived components, from low molecular mixtures derived from plant components such as vanillin, vanillic acid and protocatechuic acid, via a multistage enzyme reaction.

As a result of much diligent research in light of the current state of the art, the present inventors have completed this invention upon finding that when transformants carrying a recombinant plasmid containing a demethylase gene (vanAB gene) and benzaldehyde dehydrogenase gene (ligV gene), as well as a gene (pcaHG gene) coding for protocatechuate 3,4-dioxygenase which cleaves the protocatechuic acid ring, are cultured in the presence of vanillin or the like, the corresponding 3-carboxy-cis,cis-muconic acid molecules are produced, and further that treatment of the 3-carboxy-cis or cis-muconic acid with an acid can produce 3-carboxymuconolactone at high yield and low cost.

Specifically, the invention provides the following.
(1) A recombinant plasmid containing a vanillate demethylase gene (vanAB genes), benzaldehyde dehydrogenase gene (ligV gene) and protocatechuate 3,4-dioxygenase gene (pcaHG gene).
(2) The recombinant plasmid according to (1) above, wherein the vanAB genes are the DNA molecule set forth in SEQ ID NO: 7.
(3) The recombinant plasmid according to (1) or (2) above, wherein the ligV gene is the DNA molecule set forth in SEQ ID NO: 8.
(4) The recombinant plasmid according to any one of (1)-(3) above, wherein the pcaH gene is the DNA molecule set forth in SEQ ID NO: 1 and the pcaG gene is the DNA molecule set forth in SEQ ID NO: 3.
(5) A transformant incorporating a recombinant plasmid according to any one of (1)-(4) above.
(6) The transformant according to (5), wherein the recombinant plasmid according to any one of (1)-(4) is introduced into *Pseudomonas putida* PpY1100.
(7) A process for production of 3-carboxy-cis,cis-muconic acid and/or 3-carboxymuconolactone, characterized by culturing a transformant according to (5) or (6) above in the presence of vanillin, vanillic acid, protocatechuic acid or a mixture of two or more thereof.

According to the invention it is possible to accomplish high-yield and inexpensive fermentative production of simple 3-carboxy-cis,cis-muconic acid and/or 3-carboxymuconolactone from vanillin, vanillic acid or protocatechuic acid.

BRIEF DESCRIPTION OF THE DRAWINGS

FIG. 4 shows the conversion (12 hours) from (a): vanillin, (b): vanillic acid, (c): protocatechuic acid, (d): 3-carboxymuconolactone and (e): vanillin, the conversion (12 hours) from (f): vanillic acid and the conversion (12 hours) from (g): protocatechuic acid.

DETAILED DESCRIPTION OF THE PREFERRED EMBODIMENTS

Figure 1:
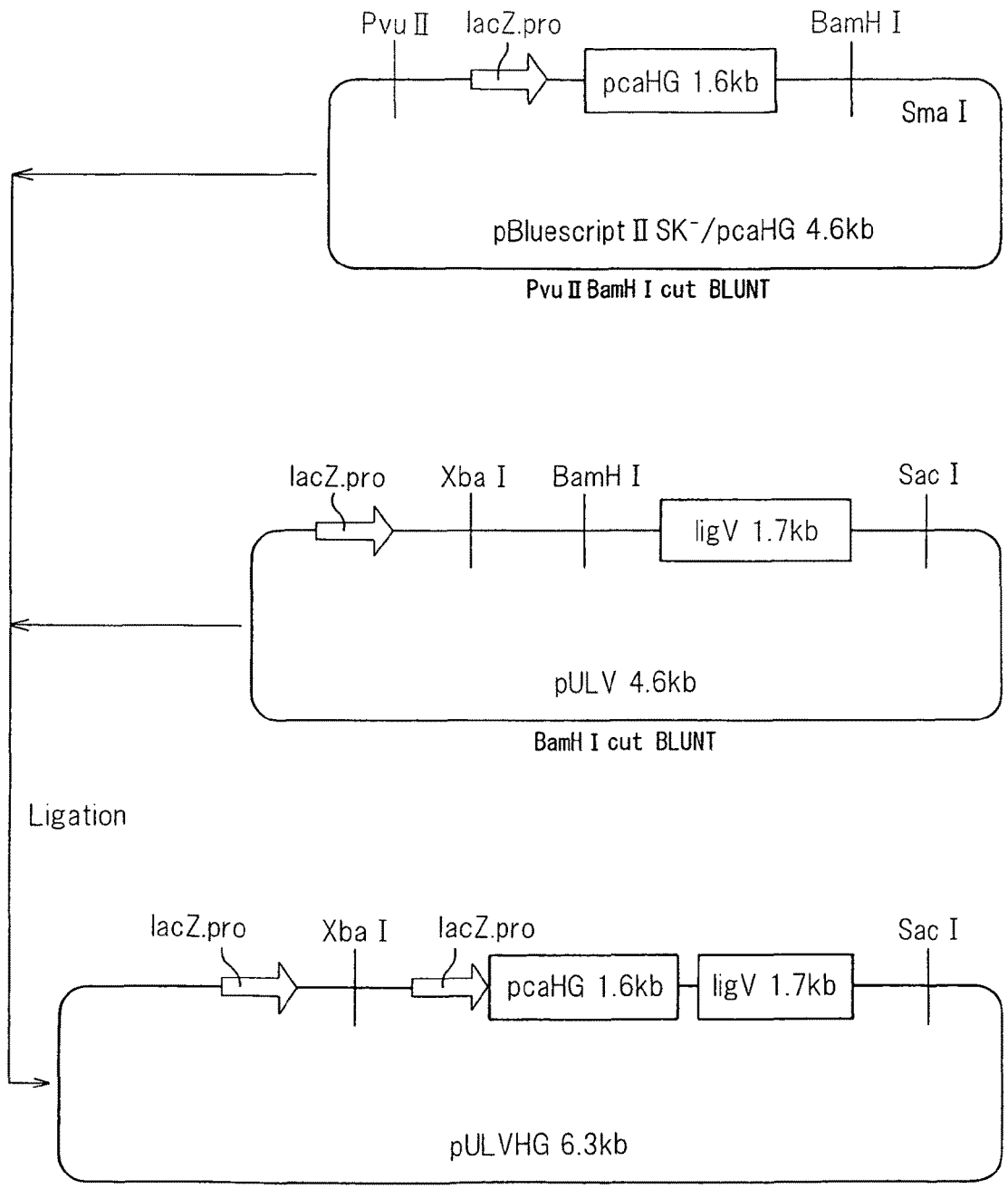
FIG. 1 is a drawing illustrating the method of constructing recombinant plasmid pULVHG.
Figure 2:
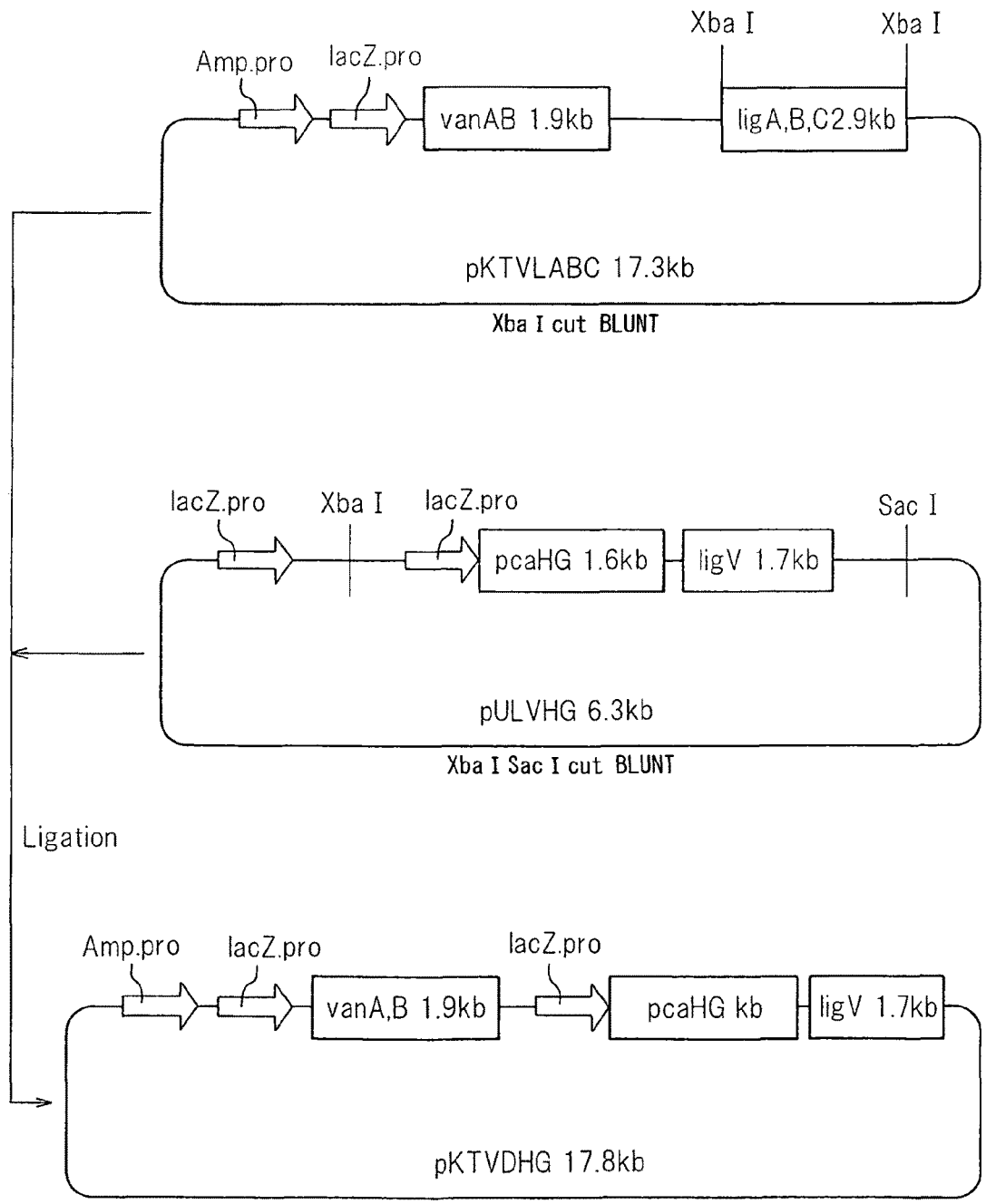
FIG. 2 is a drawing illustrating the method of constructing recombinant plasmid pKTVDHG of the invention.

Recombinant plasmid pKTVDHG of the invention is a plasmid obtained by inserting a benzaldehyde dehydrogenase gene (ligV gene) at the ligABC gene site of the known recombinant plasmid pKTVLABC (FIG. 15 of Japanese Unexamined Patent Publication (kokai) No. 2005-278549) which contains genes coding for enzymes (vanA, vanB, ligA, ligB and ligC) that catalyze a multistage process for production of 2-pyrone-4,6-dicarboxylic acid from vanillin or the like, and further downstream from it, by inserting a gene (pcaHG genes) coding for protocatechuate 3,4-dehydrogenase which cleaves protocatechuic acid rings.

Recombinant plasmid pKTVDHG of the invention has a wide host range including *Pseudomonas* bacteria, and transformants incorporating the recombinant plasmid are capable of coordinated expression of the ligV gene, vanAB genes and pcaHG genes to produce 3-carboxy-cis,cis-muconic acid and/or 3-carboxymuconolactone from either plant- or petroleum-derived or chemically synthesized vanillin, vanillic acid, protocatechuic acid or a mixture thereof.

That is, due to the presence of the pcaHG genes, protocatechuic acid is not converted to 2-pyrone-4,6-dicarboxylic acid but rather the protocatechuic acid ring is opened to yield 3-carboxy-cis,cis-muconic acid, as a precursor of 3-carboxymuconolactone.

A method for preparation of recombinant plasmid pKTVLABC is described in detail in Japanese Unexamined Patent Publication (kokai) No. 2005-278549. The vanAB genes incorporated into plasmid pKTVLABC is (i) the vanillate demethylase gene from *Pseudomonas putida* PpY101 (SEQ ID NO: 1 of said publication) or (ii) a DNA molecule coding for vanillate demethylase (SEQ ID NO: 2 and/or 3 of said publication). Preferred of these vanAB genes is the vanillate demethylase gene from *Pseudomonas putida* PpY101, which is herein set forth in SEQ ID NO: 7.

The ligV gene used for the invention may be a DNA molecule listed in Japanese Unexamined Patent Publication (kokai) No. 2005-278549, selected from among (i) the benzaldehyde dehydrogenase gene from *Sphingomonas paucimobilis* SYK-6 (SEQ ID NO: 21 of said publication), (ii) a DNA molecule coding for benzaldehyde dehydrogenase (SEQ ID NO: 22 of said publication), (iii) a DNA molecule that hybridizes under stringent conditions with the DNA molecule set forth in SEQ ID NO: 21 of said publication or a DNA molecule composed of its complementary sequence and that codes for a polypeptide with benzaldehyde dehydrogenase activity, or (iv) a DNA molecule that comprises the amino acid sequence set forth in SEQ ID NO: 22 of said publication with a deletion, substitution and/or addition of one or more amino acids and that codes for a protein with benzaldehyde dehydrogenase. Preferred of these ligV genes is the benzaldehyde dehydrogenase gene from *Sphingomonas paucimobilis* SYK-6, which is herein set forth in SEQ ID NO: 8. There are no particular restrictions on the methods of separation and fragmentation of the ligV gene from the microorganisms, and the same methods described in the aforementioned publications may be used.

The pcaHG genes used for the invention may be obtained with reference to J Bacteriol. 1989 November; 171 (11): 5915-21 or the total genome data of *Pseudomonas putida* KT2440 (NCBI accession number: NC_002947).

There are no particular restrictions on the specific method of obtaining the pcaHG genes, and as an example, the genomic DNA may be extracted from strain KT2440 and cleaved with a restriction enzyme or the like to obtain DNA fragments, and the restriction enzyme used to create restriction enzyme ends allowing insertion of the genomic DNA fragments, from vector DNA such as phage or plasmid. The recombinant vector may be constructed from the genomic DNA fragments and vector DNA using known DNA ligase. The recombinant vector may then be introduced into suitable host cells, transformants retaining the recombinant vector of interest selected and the recombinant vector of interest separated from the transformants.

The genome extraction may be accomplished by ordinary methods. For example, it is preferably accomplished by collecting cultured cells of a microorganism and, after bacteriolysis with protease K, for example, carrying out a combination of appropriate methods such as deproteinization treatment by phenol extraction, protease treatment, ribonuclease treatment, genomic DNA precipitation with an alcohol and centrifugal separation.

The plasmid used is preferably pUC18, pUC19, pUC118, pUC119, pKT230 MC, Bluescript or the like, with *E. coli* as the host. After cleavage with the restriction enzyme, the cleaved ends may be dephosphorylated as appropriate. T4 DNA ligase may be mentioned as an example of a known DNA ligase.

The nucleotide sequence of the open reading frame of the PcaH gene obtained from *Pseudomonas putida* KT2440 is set forth in SEQ ID NO: 1, its amino acid sequence is set forth in SEQ ID NO: 2, the nucleotide sequence of the reading frame of the PcaG gene is set forth in SEQ ID NO: 3 and its amino acid sequence is set forth in SEQ ID NO: 4.

The recombinant plasmid pKTVDHG of the invention may be constructed in the following manner, for example.

(1) First, a known ligase is used to link the ligV gene set forth in SEQ ID NO: 21 in Japanese Unexamined Patent Publication (kokai) No. 2005-278549 at a restriction enzyme XbaI-cleaved site within the multicloning site in a gene coding for the α fragment of LacZ located downstream from the LacZ promoter of a suitable plasmid such as Bluescript, to construct recombinant plasmid pBluescript II SK⁻/ligV.

(2) The pcaHG gene is then linked at a restriction enzyme XbaI-cleavage site in the multicloning site of a suitable plasmid to construct recombinant plasmid pBluescript II SK⁻/pcaHG.

(3) Next, a DNA fragment of a plasmid containing the LacZ promoter region, obtained by cutting of the recombinant plasmid pBluescriptII SK⁻/pcaHG with restriction enzymes PvuII and BamHI followed by end treatment, and a DNA fragment obtained by cutting of the recombinant plasmid pBluescriptII SK⁻/ligV with restriction enzyme FbaI followed by end treatment, are linked with a known ligase to construct recombinant plasmid pBluescriptII SK⁻/pcaHG-LigV. Also, a DNA fragment obtained by cutting of pBluescriptII SK⁻/pcaHG-LigV with XbaI and a DNA fragment obtained by cutting of the known recombinant plasmid pKTVLABC with restriction enzyme XbaI followed by end treatment were linked with a known ligase to construct recombinant plasmid pKTVDHG.

The microorganisms that may be used as hosts for high-yield production of 3-carboxy-cis,cis-muconic acid and/or 3-carboxymuconolactone are not particularly restricted so long as they allow replication of the recombinant plasmid of the invention and can express enzyme genes that participate in production of 3-carboxy-cis,cis-muconic acid and/or 3-carboxymuconolactone, but it is necessary to use transformants whose host is a microorganism that is permeable to plant-derived, chemically synthesized or petroleum-derived vanillin, vanillic acid or protocatechuic acid, and has lost the catabolic enzyme function from any of these to 2-pyrone-4,6-dicarboxylic acid, as well as catabolic enzyme function for 3-carboxy-cis,cis-muconic acid and/or 3-carboxymuconolactone. Preferred microorganisms of this type are *Pseudomonas* bacteria, and especially *Pseudomonas putida* PpY1100.

A known method such as a protoplast method, competent cell method or electroporation method may be used to transform the host microorganism using the recombinant plasmid.

Selection of transformants may be accomplished based on a selective marker for the plasmid used, such as drug resistance acquired by DNA recombination in the transformants. The transformants containing the recombinant plasmid of interest are preferably selected from among the transformants by colony hybridization using a partial DNA fragment of the gene as the probe. Labeling of the probe may be carried out using a radioactive isotope, digoxigenin, an enzyme or the like.

The obtained transformants may be cultured under appropriate conditions using medium containing a carbon source, a nitrogen source, metal salts, minerals, vitamins and the like. The pH of the medium may be a pH in a range that allows growth of the transformants, and the pH is preferably adjusted to about 6.0 to 8.0. The culturing conditions may be shake culturing or submerged culturing for 2 to 7 days at between 15 and 40° C. and preferably between 28 and 37° C.

The culture solution containing the 3-carboxy-cis,cis-3-muconic acid obtained by the culturing may be subjected to acid treatment for efficient conversion to 3-carboxymuconolactone. The acid used is preferably hydrochloric acid at about pH 1 to 2.

The 3-carboxy-cis,cis-muconic acid and/or 3-carboxymuconolactone obtained by the production process of the invention, as a plastic material, chemical product material or the like, can exhibit functions different from 2-pyrone-4,6-dicarboxylic acid or higher functions thereof, and therefore can serve as a useful plastic material.

EXAMPLES

The present invention will now be described in greater detail by examples, with the understanding that the invention is not limited to these examples.

Example 1

Construction of Recombinant Plasmid pKTVDHG (1) Construction of Recombinant Plasmid pKTVLABC Recombinant plasmid pKTVLABC was constructed by the method described in Japanese Unexamined Patent Publication (kokai) No. 2005-278549.

(2) Construction of Recombinant Plasmid pULV

Recombinant plasmid pULV was constructed by the method described in Japanese Unexamined Patent Publication (kokai) No. 2005-278549.

(3) Construction of Recombinant Plasmid pBluescriptII SK$^-$/pcaHG

Using the universal primer: 5'-GGTGTCAGGCAAAG-GTGTTAAGAC-3' (SEQ ID NO: 5) and reverse primer: 5'-AGTGGGGTTCTGCTGGTTCGGC-3' (SEQ ID NO: 6) as PCR primers, pcaHG was amplified from the genome of strain KT2440 and linked to a DNA fragment obtained by cleaving pBluescriptII SK with XbaI, so that it was in-frame with Lac.

(4) Construction of Recombinant Plasmid pULVHG

A DNA fragment of a plasmid containing the LacZ promoter region, obtained by cutting of the recombinant plasmid pBluescriptII SK$^-$/pcaHG with restriction enzymes PvuII and BamHI followed by end treatment, and a DNA fragment obtained by cutting of the recombinant plasmid pULV with restriction enzyme BamHI followed by end treatment, were linked with a known ligase to construct recombinant plasmid pULVHG.

(5) Construction of Recombinant Plasmid pKTVDHG

A DNA fragment obtained by cutting of pULVHG with XbaI and SacI followed by end treatment and a DNA fragment obtained by cutting of the known recombinant plasmid pKTVLABC with restriction enzyme XbaI followed by end treatment were linked with a known ligase to construct recombinant plasmid pKTVDHG.

Example 2

Production of 3-Carboxymuconolactone from Vanillin (1) Conversion from Vanillin to 3-carboxy-cis,cis-muconic Acid (1-1) Recombinant plasmid pKTVDHG constructed in Example 1 was used to transform *E. coli* HB101, and the transformants were shake cultured at 37° C. for 18 hours in LB medium (100 ml) containing 25 mg/L ampicillin, after which the recombinant plasmid pKTVDHG was extracted from the proliferated cultured cells.

(1-2) *Pseudomonas putida* PpY1100, a microorganism that has lost the catabolic enzyme function from plant-derived, chemically synthesized or petroleum-derived vanillin, syringaldehyde, vanillic acid, syringic acid, protocatechuic acid, p-hydroxybenzaldehyde or p-hydroxybenzoic acid to 2-pyrone-4,6-dicarboxylic acid, as well as catabolic enzyme function for 3-carboxymuconolactone, 3-carboxy-cis,cis-muconic acid, was cultured in 500 ml of LB liquid medium at 28° C. for 23 hours, and then cooled in ice for 30 minutes. The cells were collected by 10,000 rpm centrifugation at 4° C. for 10 minutes, and after mild rinsing with 500 ml of 0° C. distilled water, they were re-centrifuged. This was followed by additional mild rinsing with 250 ml of 0° C. distilled water and re-centrifugation. This was followed by still further mild rinsing with 125 ml of 0° C. distilled water and re-centrifugation. The collected microorganic cells were suspended in distilled water containing 10% glycerol and stored at 0° C.

(1-3) After placing 4 µl of distilled water containing about 0.05 µg of plasmid pKTVDHG DNA in a 0.2 cm cuvette, 40 µl of the cell solution suspended in distilled water containing 10% glycerol obtained in (1-2) above was added, and the mixture was subjected to electroporation under conditions of 25 µF, 2500 V, 12 msec.

(1-4) The total amount of cells obtained in (1-3) above was seeded in 10 ml of LB liquid medium and cultured at 28° C. for 6 hours. The cells were recovered by centrifugation after culturing, and then spread on an LB plate containing 25 mg/L kanamycin and cultured at 28° C. for 48 hours, and transformants carrying plasmid pKTVDHG and exhibiting kanamycin resistance were obtained. This cell line was named *Pseudomonas putida* PpY1100(pKTVDHG).

Figure 3:
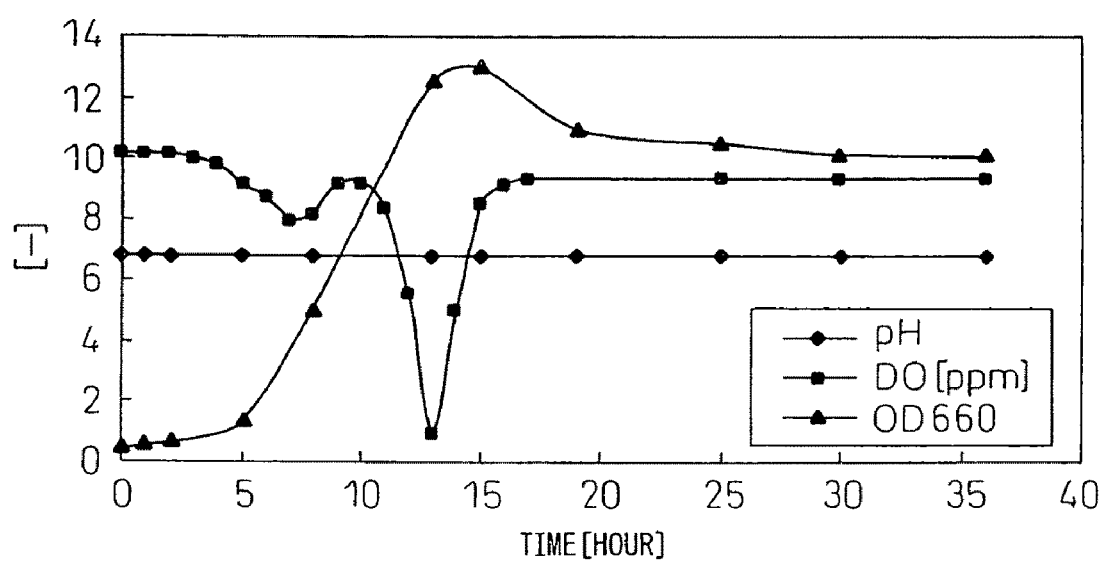
FIG. 3 is a graph showing an OD increase curve (increase in cell count) during the course of production of 3-carboxy-cis,cis-muconic acid by culturing of *Pseudomonas putida* PpY1100.

(1-5) *Pseudomonas putida* PpY1100(pKTVDHG) was seeded in 200 ml of LB liquid medium (containing 25 mg/L kanamycin) and cultured at 28° C. for 16 hours to obtain a preliminary cultured cell suspension. Next, 5 L of LB liquid medium and 3 ml of an antifoaming agent (Antiform A) were prepared using a 10 L-volume jar fermenter, and 200 ml of the preliminary cultured cell suspension of *Pseudomonas putida* PpY1100(pKTVLABC) was mixed therewith and cultured to OD660 13-14 with aerated stirring at 28° C., 500 rpm/min (10 hours-12 hours). FIG. 3 shows the OD increase curve (increase in cell volume) (—black triangle—) for production of 3-carboxy-cis,cis-muconic acid. In FIG. 3, the—black square—symbols represent oxygen concentration (81 ppm/min flow rate), and the—black diamond—symbols represent preparation to pH 6.5 with aqueous hydrochloric acid and sodium hydroxide.

(1-6) When the OD660 reached 13-14 with culturing using a 10 L-volume jar fermenter, 500 ml of culture solution was removed from the fermenter into an Erlenmeyer flask and stored on ice.

(1-7) Next, 500 ml of a 0.1 N NaOH solution (adjusted to pH 8.5) containing 50 g of vanillin as substrate was added to the culture solution in the fermenter that had reached OD660 13-14, using a peristaltic pump over a period of 5 to 7 hours. In order to prevent reduction in pH of the culture solution with production of 3-carboxy-cis,cis-muconic acid as the reaction proceeded, a 0.1 N NaOH solution was added with a peristaltic pump connected to a pH sensor to maintain the pH of the culture solution.

After 16 hours, when virtually all of the added vanillin was confirmed to have disappeared by TLC analysis, 500 ml of the ice-cooled cell suspension prepared in (1-6) above was added to the culture solution in the fermenter and culturing was continued for 12 hours. Progression of the reaction was confirmed by thin-layer chromatography (TLC).

(2) Conversion from 3-carboxy-cis,cis-muconic Acid to 3-carboxymuconolactone

Figure 4:
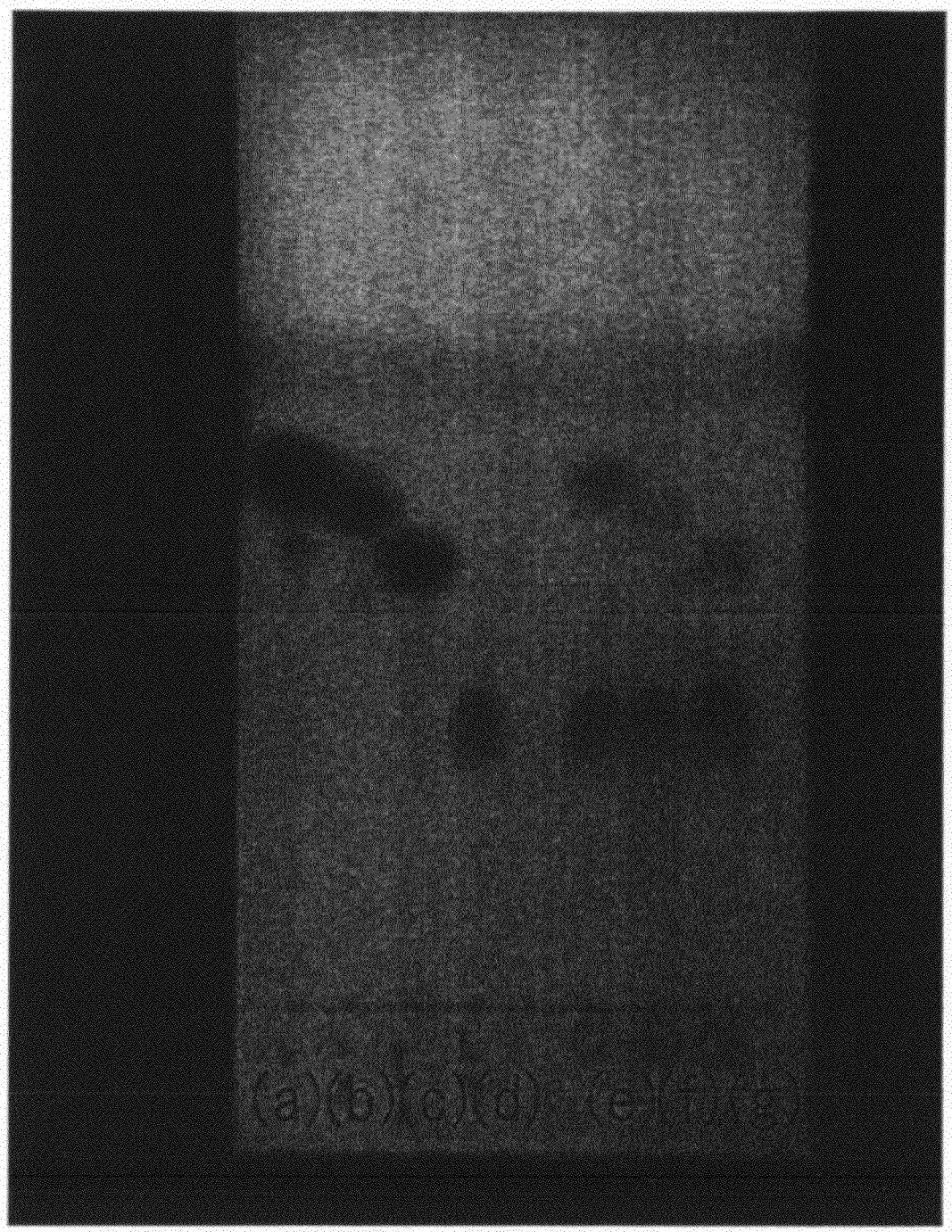
FIG. 4 is a TLC showing the course of conversion reaction from vanillin, vanillic acid or protocatechuic acid to 3-carboxy-cis,cis-muconic acid.

Upon completion of the reaction, the medium in the fermenter was transferred to a plastic container (bucket). The cell component was precipitated and removed from the culture solution by centrifugal separation (6000 rpm, 20° C.), hydrochloric acid was added to the obtained supernatant to lower the pH to below 1.0, and the mixture was stored at low temperature for conversion of the 3-carboxy-cis,cis-muconic acid to 3-carboxymuconolactone. Complete conversion to 3-carboxymuconolactone was confirmed by TLC, HPLC and GC-MS. FIG. 4(e) shows TLC with spotting of the solution extracted with ethyl acetate after hydrochloric acid treatment. After confirming complete conversion to 3-carboxymuconolactone, an organic solvent was used for extraction of the 3-carboxymuconolactone. Approximately 1.9 g of 3-carboxymuconolactone was extracted and dried from 200 ml of culture solution, which was a yield of about 88.5% as the ratio of added substrate based on the total culture solution volume of 5.7 L. The obtained 3-carboxymuconolactone was further purified by active carbon treatment or the like and the structure was confirmed by its NMR spectrum.

$^1$H-NMR (400 MHz, DMSOd$_6$) δ(ppm): 2.67, 3.10, 5.55, 6.81, 12.5-13.0

$^{13}$C-NMR (100 MHz, DMSOd$_6$) δ(ppm): 36.5, 78.5, 125.9, 157.9, 162.1, 170.4, 170.8

Ms m/z: 402 (M$^+$) (as TMS (trimethylsilyl) form of 3-carboxymuconolactone)

Example 3

Production of 3-Carboxymuconolactone from Vanillic Acid

Following the same procedure as in Example 2, except for using vanillic acid as the substrate, 3-carboxymuconolactone was obtained at a yield of about 88.5% in terms of the ratio of added substrate.

Example 4

Production of 3-Carboxymuconolactone from Protocatechuic Acid

Following the same procedure as in Example 2, except for using protocatechuic acid as the substrate, 3-carboxymuconolactone was obtained at a yield of about 88.5% in terms of the ratio of added substrate.

What is claimed is:

1. A recombinant plasmid containing a vanillate demethylase gene (vanAB gene), benzaldehyde dehydrogenase gene (ligV gene) and protocatechuate 3,4-dioxygenase gene (pcaHG gene)$_3$ wherein the pcaHG gene comprises pcaH gene and pcaG gene, and wherein pcaH gene is the DNA molecule set forth in SEQ ID NO: 1.

2. The recombinant plasmid according to claim 1, wherein the vanAB genes are the DNA molecule set forth in SEQ ID NO: 7.

3. The recombinant plasmid according to claim 1, wherein the ligV gene is the DNA molecule set forth in SEQ ID No: 8.

4. The recombinant plasmid according to claim 1, wherein the pcaG gene is the DNA molecule set forth in SEQ ID NO: 3.

5. A transformant incorporating a recombinant plasmid according to claim 1.

6. The transformant according to claim 5, wherein the recombinant plasmid according to claim 1 is introduced into *Pseudomonas putida* PpY1100.

7. A process of production of 3-carbyxy-cis, cis-muconic acid and/or 3-carboxynuconolactone, characterized by culturing a transformant according to claim 5 in the presence of vanillin, vanillic acid, protocatechuic acid or a mixture of two or more thereof.

* * * * *